US007836752B2

(12) United States Patent
Punnoose (10) Patent No.: US 7,836,752 B2
(45) Date of Patent: Nov. 23, 2010

(54) MAGNETIC GAS SENSOR AND METHODS USING ANTIFERROMAGNETIC HEMATITE NANOPARTICLES

(75) Inventor: Alex Punnoose, Boise, ID (US)

(73) Assignee: Boise State University, Boise, ID (US)

(*) Notice: Subject to any disclaimer, the term of this patent is extended or adjusted under 35 U.S.C. 154(b) by 257 days.

(21) Appl. No.: 11/964,705

(22) Filed: Dec. 26, 2007

(65) Prior Publication Data

US 2009/0133473 A1 May 28, 2009

Related U.S. Application Data

(60) Provisional application No. 60/876,810, filed on Dec. 22, 2006.

(51) Int. Cl.
G01N 9/00 (2006.01)
(52) U.S. Cl. .................................................. 73/31.05
(58) Field of Classification Search ............... 73/31.05, 73/31.06
See application file for complete search history.

(56) References Cited

U.S. PATENT DOCUMENTS

| | | | |
|---|---|---|---|
| 3,999,947 A | 12/1976 | Mihara et al. ............... 23/254 E |
| 4,045,178 A | 8/1977 | Okinaka et al. ............ 23/254 E |
| 4,457,161 A | 7/1984 | Iwanaga et al. .................. 73/23 |
| 4,458,242 A | 7/1984 | Kusanagi et al. ............. 340/634 |
| 4,703,646 A | 11/1987 | Muller et al. ..................... 73/23 |
| 4,911,892 A | 3/1990 | Grace et al. ................... 422/94 |
| 5,372,785 A | 12/1994 | Johnson et al. ................ 422/90 |
| 5,447,054 A | 9/1995 | Modica et al. .............. 73/31.06 |
| 6,246,227 B1 | 6/2001 | Hobby et al. ................. 324/204 |
| 6,270,741 B1 | 8/2001 | Inoue et al. |
| 6,481,264 B1 | 11/2002 | Williams .................... 73/31.06 |
| 6,632,402 B2 | 10/2003 | Blazewicz et al. ............. 422/84 |

(Continued)

FOREIGN PATENT DOCUMENTS

WO WO 2008/153603 12/2008

OTHER PUBLICATIONS

Watson, J. & Ihokura, K; "Gas-Sensing Materials"; MRS Bull; 24, 14-17 (1999).

(Continued)

*Primary Examiner*—Hezron Williams
*Assistant Examiner*—Nathaniel Kolb
(74) *Attorney, Agent, or Firm*—Pedersen and Company, PLLC; Ken J. Pedersen; Barbara S. Pedersen (57) ABSTRACT

A nanoscale antiferromagnetic gas sensing apparatus and methods of measuring gas using the apparatus are described. The use of the magnetic properties of an antiferromagnetic material as gas sensing parameters explores the concept of magnetic gas sensing. According to a preferred embodiment, a nanoscale magnetic hydrogen sensor apparatus is developed based on varying of the saturation magnetization and remanence of nanoscale antiferromagnetic hematite with hydrogen flow. For example, the saturation magnetization and remanence of nanoscale hematite has been shown to increase one to two orders of magnitude in the presence of flowing hydrogen gas at concentrations in the 1-10% range and at 575 K, indicating that a magnetic hydrogen sensor using hematite material may be practical and useful for detecting hydrogen in various environments such as those wherein production, storage, transportation, and/or vehicle use of hydrogen is being conducted.

12 Claims, 9 Drawing Sheets

U.S. PATENT DOCUMENTS

| | | | | |
|---|---|---|---|---|
| 6,668,627 | B2 | 12/2003 | Lange et al. | 73/105 |
| 6,996,478 | B2 | 2/2006 | Sunshine et al. | 702/22 |
| 2003/0153088 | A1* | 8/2003 | DiMeo et al. | 436/113 |
| 2005/0100930 | A1 | 5/2005 | Wang et al. | |
| 2006/0060776 | A1 | 3/2006 | Punnoose | |

OTHER PUBLICATIONS

Baughman, R.H. Zakhidov, A.A. & de Heer, W.A.; "Carbon Nanotubes—The Route Toward Applications"; Science 297, 787-792 (2002).

Modi, A., Koratkar, N., Lass, E., Wei, B & Ajayna, P.M.; "Miniaturized Gas Ionization Sensors Using Carbon Nanotubes"; Nature 424, 171-174 (2003).

Miasik, J.J., Hooper, A. & Tofield, B.C.; "Conducting Polymer Gas Sensors"; J. Chem. Soc. Faraday Trans. 182, 1117-1126 (1986).

Matsubara, S., Kaneko, S., Morimoto, S., Shimizau, S., Ishihara, T. & Takita, Y.; "A Practical Capacitive Type CO2 Sensor Using Ce02/BaCO3/CuO Ceramics"; Sens. Actuators B 65, 128-132 (2000).

Shimizu, Y. & Egashira, M.; "Basic Aspects and Challenges of Semiconductor Gas Sensors"; MRS Bull. 24, 18-24 (1999).

Moseley, P.T.; "Materials Selection for Semiconductor Gas Sensors"; Sens Actuators B 6, 149-156 (1992).

Tadeev, A.V., Delabouglise, G. & Labeau, M.; "Influence of Pd and Pt additives on the Microstructural and Electrical Properties of SnO2-Based Sensors"; Mater. Sci. Eng. B 57, 76-83 (1998).

Xu, C., Tamaki, J., Miura, N. & Yamazoe, N.; "Correlation Between Gas Sensitivity and Crystallite Size in Porous SnO2-Based Sensors"; Chem. Lett., 441-442 (1990).

Gopal Reddy, C.V. & Manorama, S.V.; "Room Temperature Hydrogen Sensor Based on SnO2:La2O3"; J. Electrochem. Soc. 147/1, 390-393 (2000).

Punnoose, A., Magnone, H., Seehra, M.S. & Bonevich, J.; "Bulk to Nanoscale Magnetism and Exchange Bias in CuO Nanoparticles"; Phys. Rev. B 64, 174420-1-174420-8 (2001).

Punnoose, A., Seehra, M., Shah, N., Phanthavady, T. & Huffman, G.P.; "Magnetic properties of Ferrihydrite Nanoparticles Doped With Ni, Mo and Ir"; Phys. Rev B 69, 054425-1-054425-9 (2004).

Kodama, R.H. & Berkowitz, A.E.; "Atomic-Scale Magnetic Modeling of Oxide Nanoparticles"; Phys. Rev. B 59, 6321-6326 (1999).

Punnoose, A., Reddy, K.M., Thurber, Aaron, Hays, Jason, and Engelhard, Mark H.; "Novel magnetic Hydrogen Sensing: A Case Study Using Antiferromagnetic Hematite Nanoparticles"; Nanotechnology 18; Published Mar. 23, 2007.

Madsen, Morup, and Hansen; "On the interpretation of magnetization data for antiferromagnetic nanoparticles". Journal of Magnetism and Magnetic Materials 305, 95-99 (2006). Available online Dec. 21, 2005.

Ponzoni, Andrea, Comini, Elizabetta, and Sberveglieri, Giorgio; "Ultrasensitive and highly selective gas sensors using three-dimensional tungsten oxide nanowire networks"; Applied Physics Letters 88, 203101 (2006) Published online May 15, 2006.

Comini, E., Faglia, G., and Sberveglieri, G.; "Stable and highly sensitive gas sensors based on semiconducting oxide nanobelts", Applied Physics Letters vol. 81, No. 10, Sep. 2, 2002.

PCT International Search Report, Applicants Boise State University and Punnoose (in U.S.), PCT/US2007/88864, relating to PCT Publication WO 2008/153603, Sep. 26, 2008.

* cited by examiner

NO GAS

Fig. 4C

H₂ FLOW

MAGNETIC GAS SENSOR AND METHODS USING ANTIFERROMAGNETIC HEMATITE NANOPARTICLES

This application claims priority of U.S. Provisional Application 60/876,810, filed Dec. 22, 2006, the entire disclosure of which is incorporated herein by this reference.

BACKGROUND OF THE INVENTION

1. Field of the Invention

The invention relates to hydrogen sensors, and, particularly, to nanoscale antiferromagnetic hematite sensors.

2. Related Art

Hydrogen sensing is a critical component of safety necessary to address widespread public perceptions of the hazards of production, storage, transportation and use of hydrogen in proposed future automobiles and in various other applications. The need to detect leaks from hydrogen-powered cars long before the gas becomes an explosive hazard (<4% $H_2$ in air) makes it necessary to develop such sensors to be small enough to be incorporated into the vehicles' engines as well as suitable for operation in highly mobile environments. Commercial solid-state gas sensors employing the electrical properties of oxide semiconductors suffer from low sensitivity, serious difficulties associated with complex electrical contacts especially when used in mobile environments, and degradation of the material surface and electrical contacts when used in reactive chemical environments.

Since oxygen vacancies are primarily produced on the surface of the particles/films, the inventor proposes that a way to significantly improve gas sensitivity is to develop new methods that utilize the high surface area of particles produced in the nanoscale form. However, nanoscale powders with very large surface-to-volume ratios cannot be used in the conventional electrical-property-based sensing methods because stable electrical contacts are extremely difficult to make on powders and nanoparticles. Therefore, there is still a need for an effective nanoscale hydrogen gas sensor that overcomes these problems.

The present invention meets the need for a nanoscale hydrogen sensor. Preferred embodiments exhibit varying saturation magnetization and remanence of nanoscale antiferromagnetic hematite with increasing concentration of hydrogen gas, and, thus, facilitate the magnetic properties to be used as novel gas sensing parameters. A magnetic hydrogen sensor employing changes in the magnetic force experienced by a magnetized metal nonorod as a result of changes in the sample magnetization of a nanoscale hematite powder is described.

SUMMARY OF THE INVENTION

The present invention comprises nanoscale antiferromagnetic gas sensing apparatus and methods of measuring gas using said apparatus. The present invention comprises the use of the magnetic properties of an antiferromagnetic material as gas sensing parameters, thus exploring the concept of "magnetic gas sensing". Preferred embodiments comprise nanoscale magnetic hydrogen sensor apparatus based on varying of the saturation magnetization and remanence of nanoscale antiferromagnetic hematite with hydrogen flow. For example, the saturation magnetization and remanence of nanoscale hematite has been shown to increase one to two orders of magnitude in the presence of flowing hydrogen gas at concentrations in the 1-10% range and at 575 K, indicating that a magnetic hydrogen sensor using hematite material may be practical and useful for detecting hydrogen in various environments such as those wherein production, storage, transportation, and/or vehicle use of hydrogen is being conducted.

BRIEF DESCRIPTION OF THE DRAWINGS

FIG. 3 is an additional set of graphs showing results from experimentation using the set-up of FIG. 1. In FIG. 3, up-arrows represent the introduction of $H_2$ into the chamber and down-arrows represent when $H_2$ flow is ceased.

DETAILED DESCRIPTION OF THE INVENTION

Referring to the figures, there is shown one, but not the only, embodiment of the invented apparatus and/or methods for sensing gas, and, in preferred embodiments, for sensing hydrogen. The need to detect leaks from hydrogen-powered machinery long before the gas becomes an explosive hazard makes it necessary to develop such sensors. The most important requirement for a practically useful hydrogen sensor is the ability to quickly respond to the presence of hydrogen well before the explosive limit of 4% $H_2$ in the air. Conventional sensors employ the systematic dependence of the electrical properties of oxide references, and hence are electrical-property-based sensors. However, such conventional sensors suffer from low sensitivity, serious difficulties associated with complex electrical contacts especially when used in mobile environments and degradation of the material surface, and electrical contacts when used in reactive chemical environments.

The use of nanoparticles with very large surface-to-volume ratios can significantly improve the gas sensitivity because of the oxygen vacancies that are primarily produced on the surface. Therefore, the development of new hydrogen sensing methods, which can effectively utilize the high surface area of nanoscale particles, is an important task that this invention addresses. This will allow the rapid miniaturization of current bulky hydrogen sensors, allowing them to be used in mobile micro- and nano-scale devices capable of being employed in hydrogen-fueled automobiles. Since hydrogen is detected based on its reducing ability, any reducing gas may be detectable with improved sensitivity using these nanoscale gas sensors and this might increase the applicability of the gas sensing method far beyond the automobile hydrogen sensors.

Bulk antiferrogmagnets are magnetically-inactive materials due to the antiparallel arrangement of spins. Antiferromagnetic (AF) ordering in nanoscale oxides, such as hematite ($\alpha$-$Fe_2O_3$), results from the superexchange interaction between the $Fe^{3+}$ spins mediated by intervening oxygen ions. This indicates that the removal of a fraction of the oxygen ions from an AF oxide might results in an increased magnetization due to the additional uncompensated spins produced near the oxygen vacancies. The exact magnitudes of the magnetic parameters therefore could vary with oxygen stoichiometry. It has been well established that the oxygen stoichiometry of oxides can be altered by passing oxidizing or reducing gases through the sample, which forms the basis for conventional gas sensors, employing changes in the electrical properties of semiconductor oxides with oxygen stoichiometry.

In preferred embodiments of the present invention, by monitoring the changes in the magnetic properties of a nanoscale AF oxide, the presence and changes in the concentration of reactive gases, especially hydrogen, in the sample neighborhood can be detected and estimated. Therefore, the inventor believes that magnetic hydrogen sensing apparatus, employing the magnetic properties of an AF oxide in the sensing parameters, may be used for various gas sensing applications, and importantly, for hydrogen gas sensing. Such magnetic hydrogen sensors will eliminate the difficulties associated with making good electrical contacts in micro and nanoscale gas sensing components, especially when attached to moving devices. Since magnetic response is much faster than electrical response, magnetic hydrogen sensors will respond more quickly so that corrective action can occur before the explosive limit is reached. The operating temperature range of the magnetic hydrogen sensors can be as high as the magnetic ordering temperature (850 K for $\alpha$-$Fe^2O^3$) of the sample material incorporated into the sensor.

Experimental Details

Figure 1:
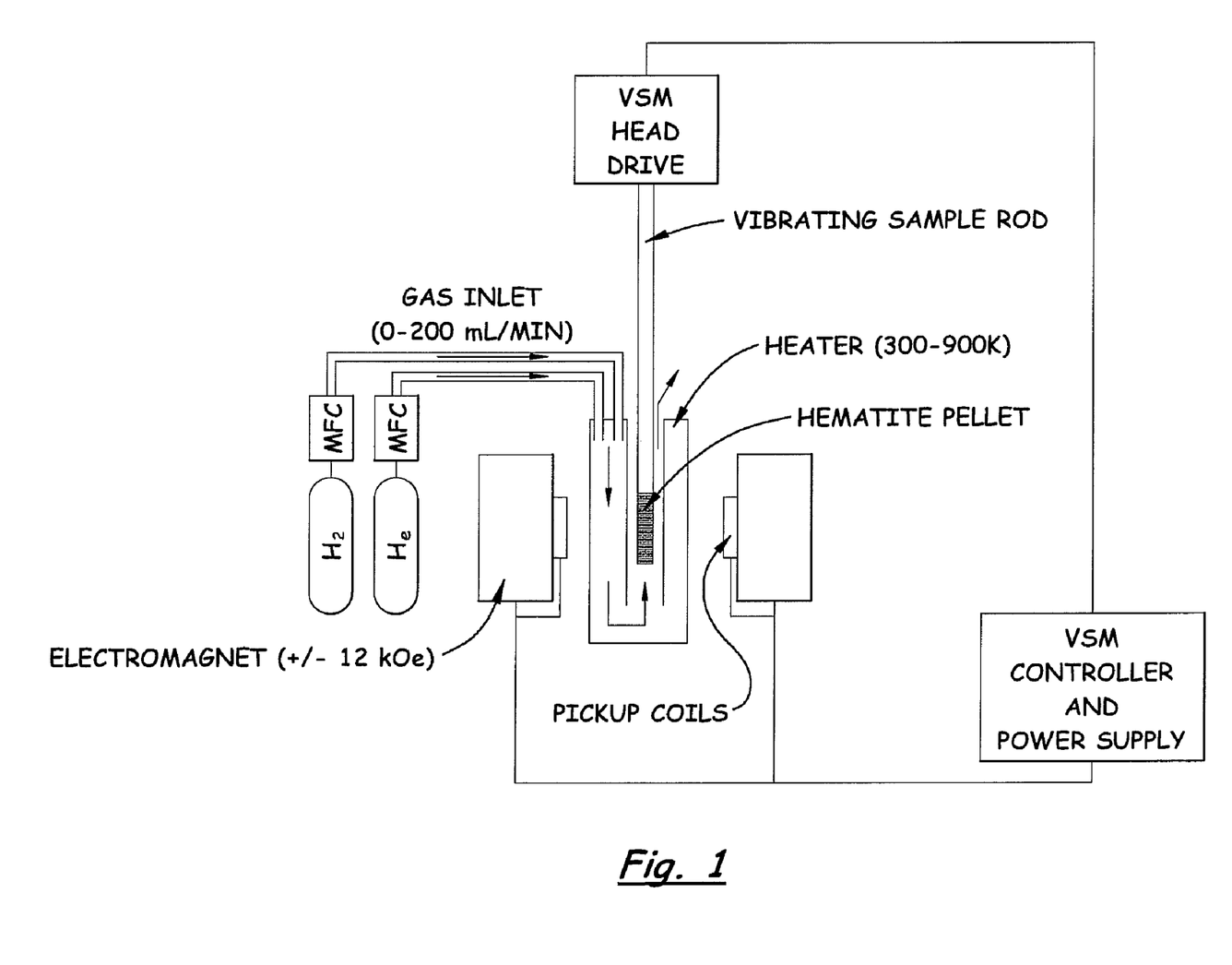
FIG. 1 is a schematic diagram of one embodiment of the magnetic gas sensing experimental set-up of the present invention.

The experimental set-up employed to conduct the magnetic hydrogen sensing measurements, given in FIG. 1, consisted of a commercial (Lakeshore Model 7404) vibrating sample magnetometer (VSM) capable of producing magnetic fields, H, up to +/− 12 kOe. A high temperature (300-900 K) oven is built into this unit with options for controlled hydrogen flow to allow the measurement of the magnetic properties as a function of gas flow rate/time, temperature and magnetic field. A combination of two mass flow controllers allowed the determination of the hydrogen concentration and flow rates accurately. For reasons of experimental convenience, the hydrogen sensing measurements were carried out on 6 mm×0.5 mm sized pellets of chemically synthesized $Fe_2O_3$ nanoparticles of size ~250 nm as determined from transmission electron microscopy. Additionally, thermogravimetric analysis (TGA) was carried out using a Thermal Advantage Q600 to establish oxygen loss when hydrogen was introduced near a $Fe_2O_3$ pellet. The starting weight of the sample when first loaded into the TGA at room temperature was taken as 100%. For the gas sensing experiments utilizing the TGA and VSM, a steady flow of ~20 ml/min) comprises reactive gases like $H_2$ and inert gases like He for dilution and were introduced and removed periodically at times indicated by arrows in the figures. The sample chambers in both the TGA and VSM systems were open to air on one side maintaining atmospheric pressure and the He purge flow was and is not expected to block air ingress into the sample area.

Results and Discussion

Figure 2A:
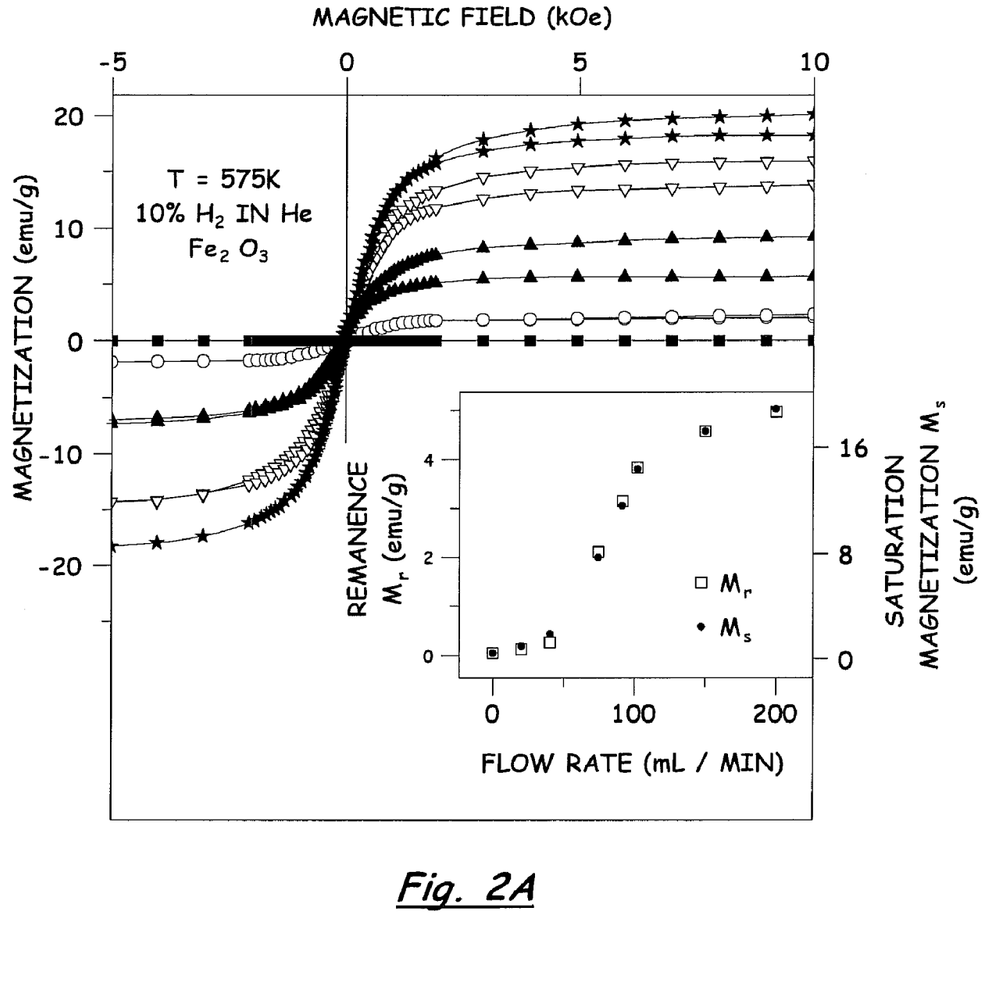
FIG. 2 is a set of graphs showing results from experimentation using the set-up of FIG. 1, wherein the upper graph is FIG. 2a and the lower graph is FIG. 2b.
Figure 2B:
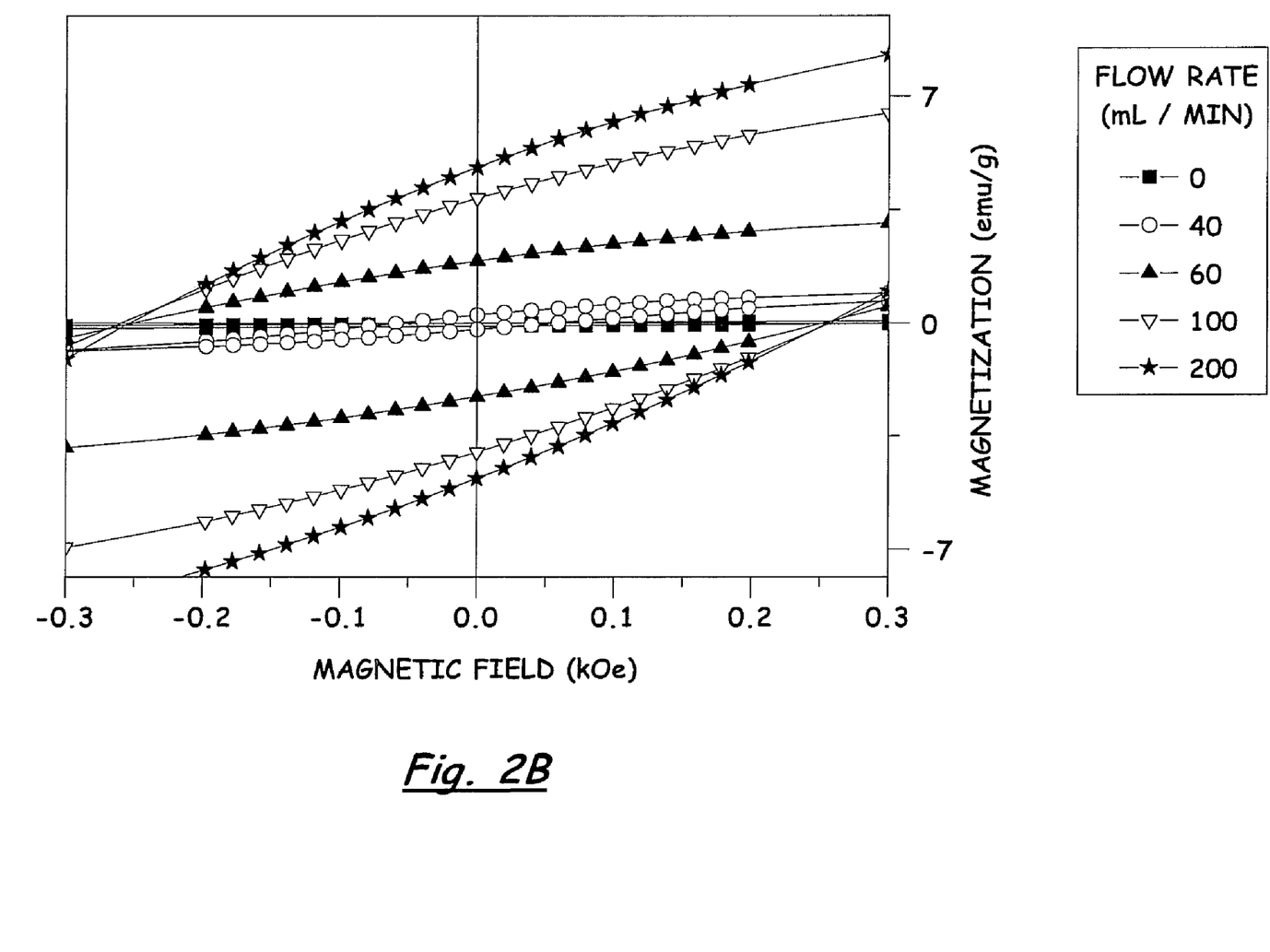

The room-temperature hysteresis loop of the fresh $Fe_2O_3$ sample measured in air showed a saturation magnetization $M_s$=0.30 emu/g, coercive field $H_c$=60 Oe and remanent magnetization $M_r$=0.10 emu/g. Flowing 10% hydrogen in helium gas (0 to 200 ml/min) across the sample that was maintained at room temperature did not show any measurable change in the magnetic parameters. As the sample temperature increased, significant changes in the hysteresis loop parameters were observed. FIG. 2a shows hysteresis loops illustrating the changes in the saturation magnetization $M_s$ of $Fe_2O_3$ with the gas flow rate at 575 K. FIG. 2b shows the low field region illustrating the variation of remanent magnetization $M_r$ and coercive field $H_c$ of $Fe_2O_3$ with hydrogen flow rate. The inset in FIG. 2a shows the variation of the magnetic properties $M_r$ and $M_s$ of the $Fe_2O_3$ sample with hydrogen gas flow, measured at 575 K.

The hysteresis loops, measured at 575 K as a function of varying hydrogen flow rates, showed a systematic increase in $M_s$ with increasing flow rates of hydrogen gas (FIG. 2a). The remanence $M_r$ also increased systematically with the hydrogen flow rate (FIG. 2b). The observed variations in $M_s$ and $M_r$ of the $Fe_2O_3$ samples as a function of hydrogen gas flow rate measured at 575 K are shown as the inset of FIG. 2a. This clearly establishes the fact that the ferromagnetic parameters $M_s$ and $M_r$ indeed can act as hydrogen sensing parameters, with the appropriate calibration. The coercive field increased from 60 to 250 Oe for 60 ml/min and did not show any further change with increased gas flow. However, the saturation magnetization increased from 0.30 emu/g to 18 emu/g and remanent magnetization from 0.10 emu/g to 6 emu/g with the flow rate varying from 0 to 200 ml/min (10% $H_2$ in He).

Figure 3A:
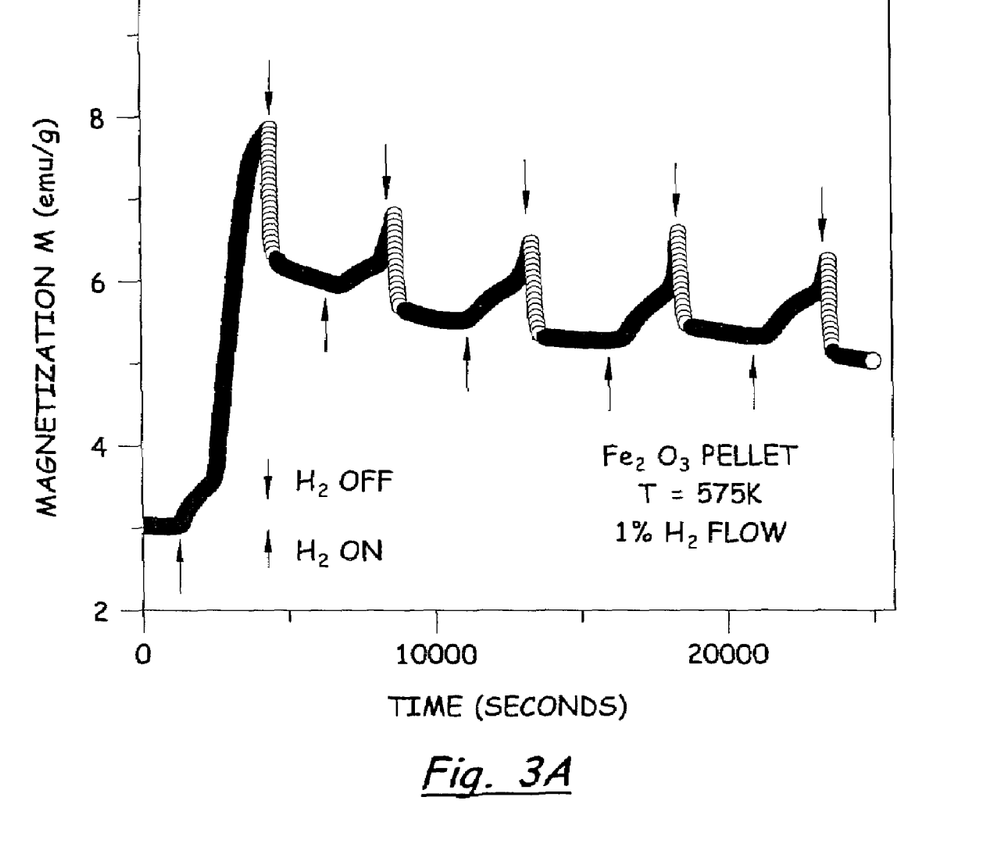
FIG. 3a shows magnetic response of a $Fe_2O_3$ pellet when subjected to a periodic 1% $H_2$ flow at 575 degrees K. Magnetization increases when $H_2$ is introduced then restores back when $H_2$ flow has ceased, confirming the reversible nature of the process.
Figure 3B:
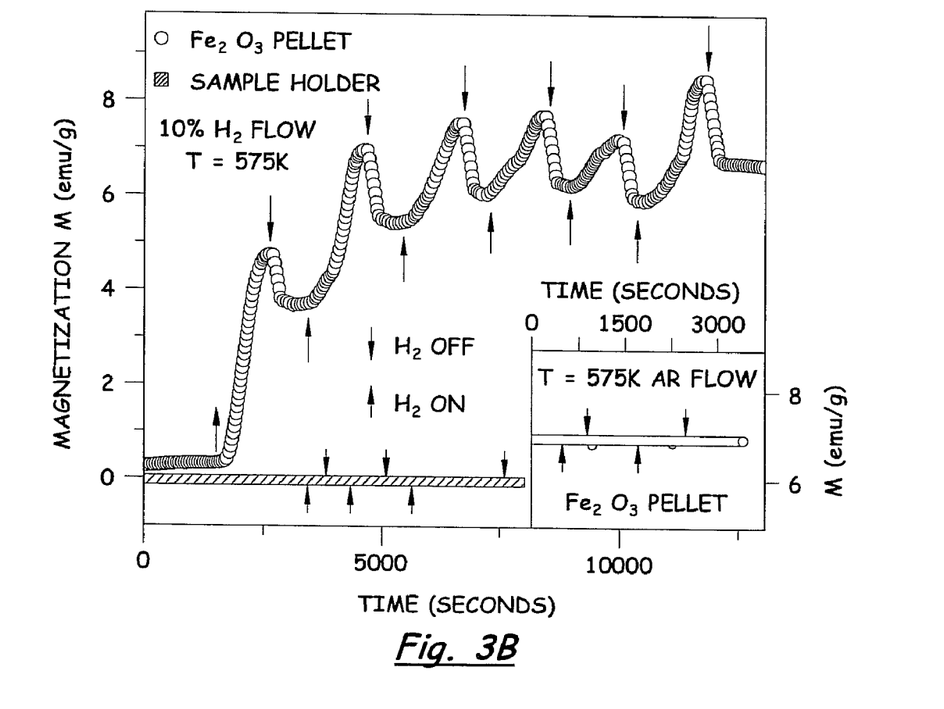
FIG. 3b shows magnetic response of a $Fe_2O_3$ pellet (open circles in FIG. 3b) and the empty sample holder (solid squares) when subjected to a periodic 10% $H_2$ flow at 575 degrees K. The inset in FIG. 3b shows the magnetization response of the sample when Ar is used in place of $H_2$.

FIGS. 3a and 3b show the magnetic response characteristics of the hematite sample in 1% and 10% $H_2$ atmospheres, respectively. The sample magnetization increases rapidly as soon as the $H_2$ flow of 150 ml min$^{-1}$ was introduced into the sample chamber. Once the $H_2$ flow was stopped, the magnetization of the materials dropped. This was done several times to verify that the effect was consistent over a period of time. This data shows the reversible nature of the gas-induced magnetic changes of hematite, a very essential feature for practical gas sensors. Two control experiments were also conducted to confirm the role of hematite and hydrogen gas in the sensing process. First, the response experiment with 10% $H_2$ shown in FIG. 3b was repeated under identical conditions after removing the hematite (using just the sample holder and adhesive putty). No magnetic response was observed as shown in FIG. 3b, confirming that the observed magnetic gas sensing effect results from hematite. Second, an experiment identical to that shown in FIG. 3b, but replacing 10% $H_2$ with Ar, was then conducted. As illustrated in the inset of FIG. 3b, no gas-induced magnetic changes were observed in this case, confirming the role of hydrogen gas in changing the magnetic response.

The most crucial result that will decide the use of a hydrogen sensing method is its ability to detect gas at concentrations well below the explosive limit of 4% $H_2$ and its ability to respond very quickly to changes in the hydrogen environment. To determine the response characteristics of the $Fe_2O_3$, magnetization was recorded over a period of time during which hydrogen gas (at a flow rate of 200 ml/min, but with only 1% $H_2$ in He) was intermittently added and removed. As shown in FIG. 3a, the sample magnetization increases rapidly as hydrogen gas is introduced into the measuring chamber. In other words, FIG. 3a confirms a strong magnetic response when the $Fe_2O_3$ sample was subjected to 1% hydrogen, thus demonstrating that this magnetic gas sensing process is suitable for practical applications. Once the hydrogen flow was shut off, the magnetization of the material dropped and this effect was consistent over a period of time. This confirms a strong response as well as the reversible nature of the magnetic properties of the $Fe_2O_3$ sample with changing atmosphere. However, the response time is longer than desired. Also, each time hydrogen flow is introduced into the measuring chamber, the magnetic response is relatively slower than the response observed when the flow is stopped. The overall slower response and this difference in response times are believed to be related to the complexities associated with the experimental setup, such as (i) the long gas flow tubes connecting the sample chamber and the gas cylinder, (ii) the use of the hematite sample in hard pressed pellet form causing the hydrogen gas to diffuse very slowly into the interior of the pellet, (iii) the large size and complex structure of the sample chamber, and (iv) the vibration based VSM detection process. Despite this fact, however, the experimental data shown in FIG. 3a demonstrates that the new magnetic hydrogen sensing method is sensitive to leaks with concentrations well below the explosive limits of 4%, and the experimental setup employed in this work responded to $H_2$ concentrations as low as 1%. Thus, it is shown that magnetic hydrogen sensing meets the essential features for practical conditions and that with continued development of the sensing material and detection methods, superior hydrogen sensors can be developed for the first time employing the magnetic property of a material.

Figure 3C:
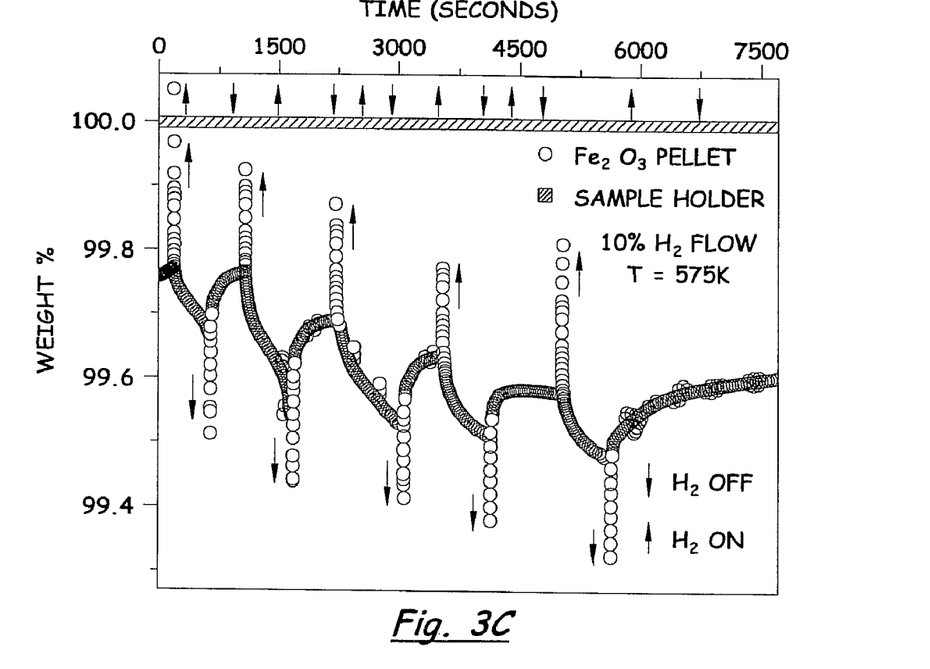
FIG. 3c shows mass response of the $Fe_2O_3$ pellet (open circles) and the empty sample holder (open triangles) when subjected to a periodic 10% $H_2$ flow at 575 degrees K in a thermogravimetric analyzer. As $H_2$ is introduced into the furnace, mass decreases and when the $H_2$ flow is stopped, mass increases. The sharp spikes in the data observed during haematite measurement are also observed in the data obtained from a run with just the sample holder. The spikes in both cases have similar widths, indicating that they may arise due to the TGA balance response in different gas flow rates.
Figure 4A:
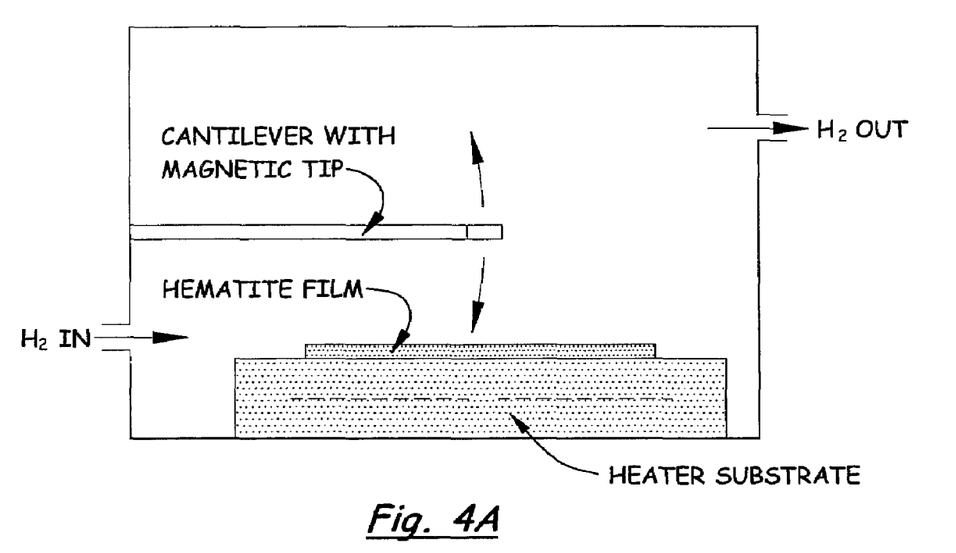
FIG. 4 is a schematic example of a proposed commercial magnetic hydrogen sensor according to an embodiment of the present invention.
Figure 4B:
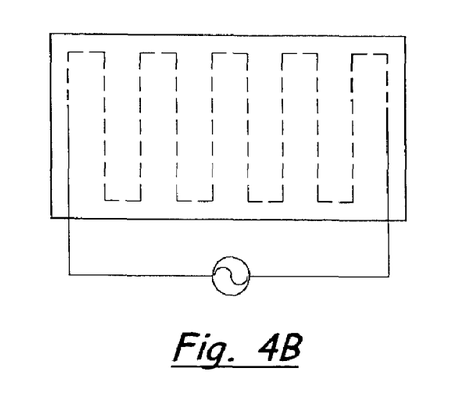
Figure 4C:
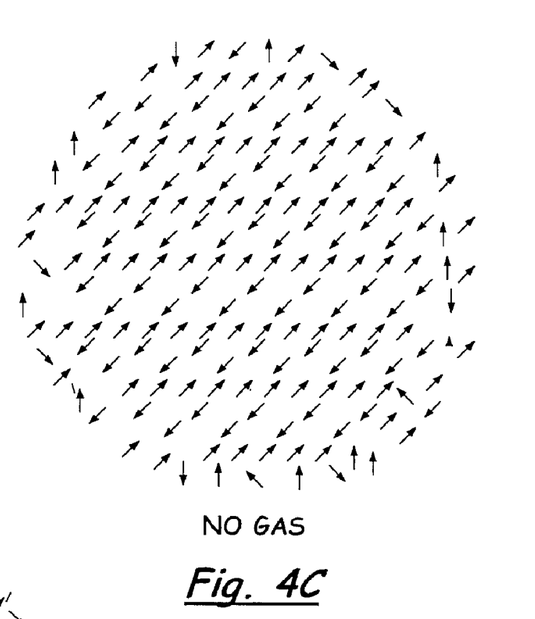
Figure 4D:
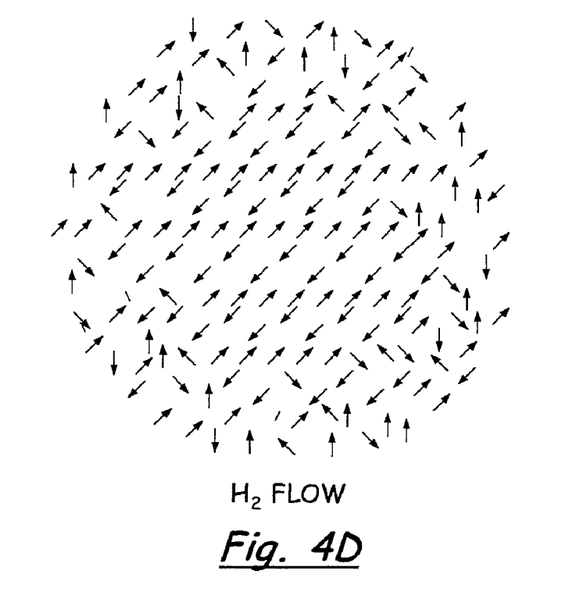

FIG. 3c shows the changes in the sample mass in response to the 10% $H_2$ gas in a thermogravimetric analyzer (TGA). When the hydrogen gas is introduced into the sample chamber, the mass of the sample drops by approximately 0.13% as the $H_2$ flow reduces the oxygen content of the $Fe_2O_3$, generating $Fe_2O_{3-\delta}$. This is followed by an average mass gain of about 0.11% when the $H_2$ flow is ceased. The cause for the mass gain being slightly lower than the mass loss is likely due to a fraction of oxygen vacancies not being replenished when the hydrogen flow is turned off. The mass recovery is much faster than the mass loss (FIG. 3c) and this is similar to the differences in the magnetic response (see FIGS. 3a and 3b) of the samples. The TGA setup employs a continuous purge gas of helium to protect the balance assembly and might add to this effect. The 20 ml/min He purge flow will not completely deplete the oxygen/air presence from the sample area and will allow sufficient oxygen ions for the observed mass recovery. Such differences are not uncommon in the gas response of the metal oxides and many of the factors mentioned to account for a similar difference in the magnetic response may be valid here also; further study may be needed to completely understand the exact mechanism behind this difference. The $Fe_2O_3$ sample showed a slight improvement in the magnetic properties after the hydrogen treatment, presumable due to these residual oxygen vacancies that were not replenished upon cooling to room temperature. However, these changes are indeed much smaller in magnitude compared to the changes observed when measurement were made in situ at 575 K with flowing hydrogen. The TGA results shown in FIG. 3c indicate that the hydrogen atmosphere plays an important role in altering the oxygen vacancies, which is responsible for the orders of magnitude changes in the observed magnetic properties of $Fe_2O_3$. The observed increase in magnetic properties, especially $M_s$, with hydrogen flow indicates that oxygen vacancies produce uncompensated spins in the AF $Fe_2O_3$ particles. Thus, the increased number of oxygen vacancies is responsible for the observed increase in magnetization. When semiconductor oxides interact with hydrogen, surface adsorption of ions/molecules is also a possibility. Such surface-adsorbed molecules can change the electronic structure at the surface, and the overall magnetic behavior of the material. However, the TGA data demonstrating a mass loss when $H_2$ is introduced into the sample chamber favors the oxygen removal process over the surface adsorption possibility.

The results described here, based on experiments employing a vibrating sample magnetometer and hematite as a test sample, are put forth to establish the basic scientific concept of magnetic hydrogen sensing. The VSM equipment is very bulky and the method takes some time in signal averaging and amplifying. However, for practical applications, much simpler and smaller detection methods may be needed and the response time needs to be improved by developing more rapid detection methods. Since the saturation magnetization and remanent magnetization of the hematite pellet displayed one to two orders of magnitude increase with $H_2$ flow at 575 K, much simpler, faster and more efficient practical magnetic hydrogen sensor could be developed employing other simpler methods of magnetic detection. In FIG. 4, an example of such a simple magnetic hydrogen sensor employing changes in the magnetic force experienced by a magnetized metal nanorod as a result of the changes in the sample magnetization of a nanoscale $Fe_2O_3$ powder (spin coated on a substrate) maintained at 575 K is illustrated. FIG. 4 shows an example of a proposed commercial magnetic hydrogen sensor (top left panel) employing changes in the magnetic force experienced by a magnetized material as a result of the changes in the sample magnetization of nanoscale $Fe_2O_3$ when hydrogen is present. The top right panel shows the detailed view of the sample film and its temperature-controlled sample holder. The lower panel (from left to right) shows the suggested mechanism of the sensing process: increased oxygen loss-defects in the surface region of the particles during $H_2$ flow increases the uncompensated surface spins causing increased ferromagnetic-like magnetization. Compared to the VSM method which measures the change in the magnetization of the entire sample, this method depends on the magnetization change on the surface of the sample. Therefore, the response is expected to be much stronger and faster than the VSM based results presented earlier.

Figure 5:
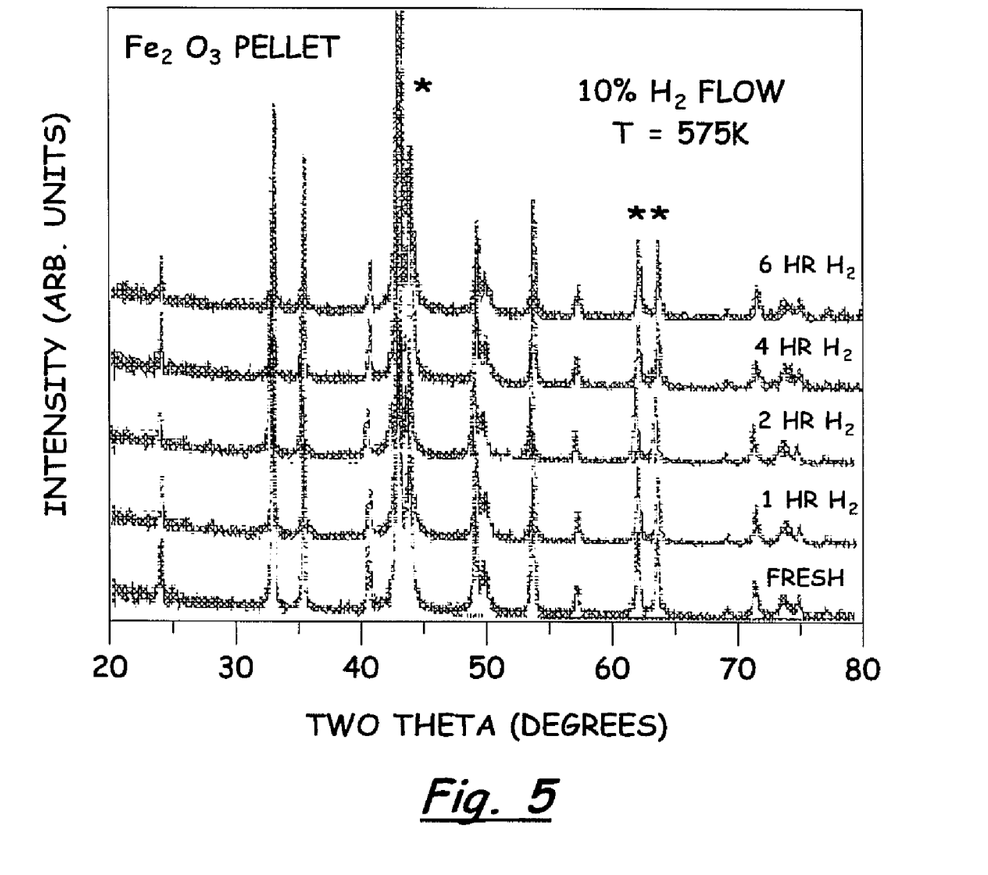
FIG. 5 is a set of X-ray diffraction (XRD) patterns of a hematite pellet using in the experimental set-up of FIG. 1.

The structural and chemical stability of the $Fe_2O_3$ sample to the hydrogen treatment was investigated by the detailed x-ray diffraction (XRD) and the x-ray photoelectron spectroscopy (XPS) studies performed before and after the hydrogen treatment. FIG. 5 shows X-ray diffraction patterns recorded on the $Fe_2O_3$ pellet before and after H2 gas sensing. The peaks marked with an asterisk (*) are from the sample holder. The XRD spectrum of the fresh sample (FIG. 5) showed well-defined peaks due to all the expected crystal planes of pure naemative. The XRD spectra were also taken after subjecting the sample to 10% hydrogen atmosphere for 1, 2, 4 and 6 hours. These XRD patterns shown in FIG. 5 did not shown any noticeable changes, thus ruling out any structural or chemical phase change.

Figure 6A:
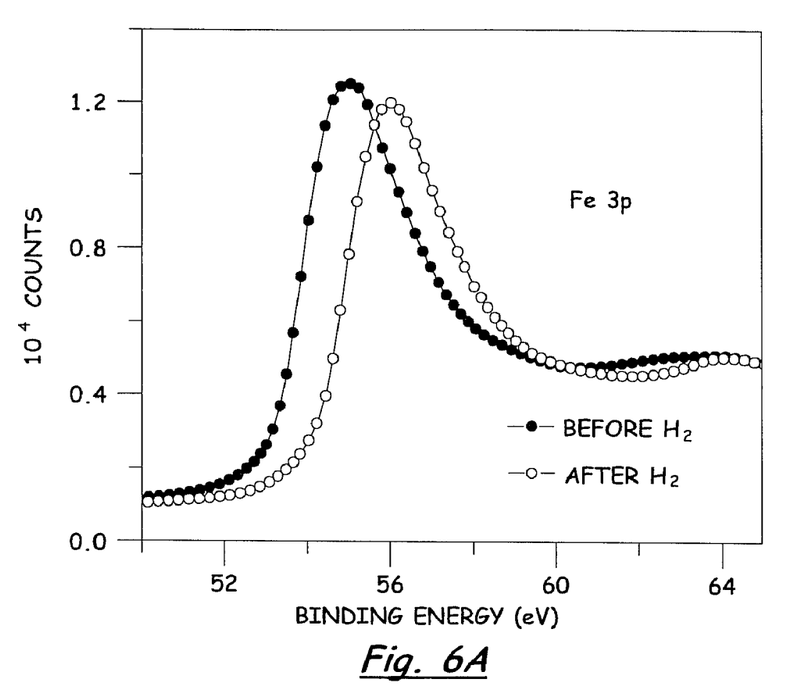
FIG. 6 is a set of X-ray photoelectron spectroscopy (XPS) data graphs of the pellet used in FIGS. 1 and 5.
Figure 6B:
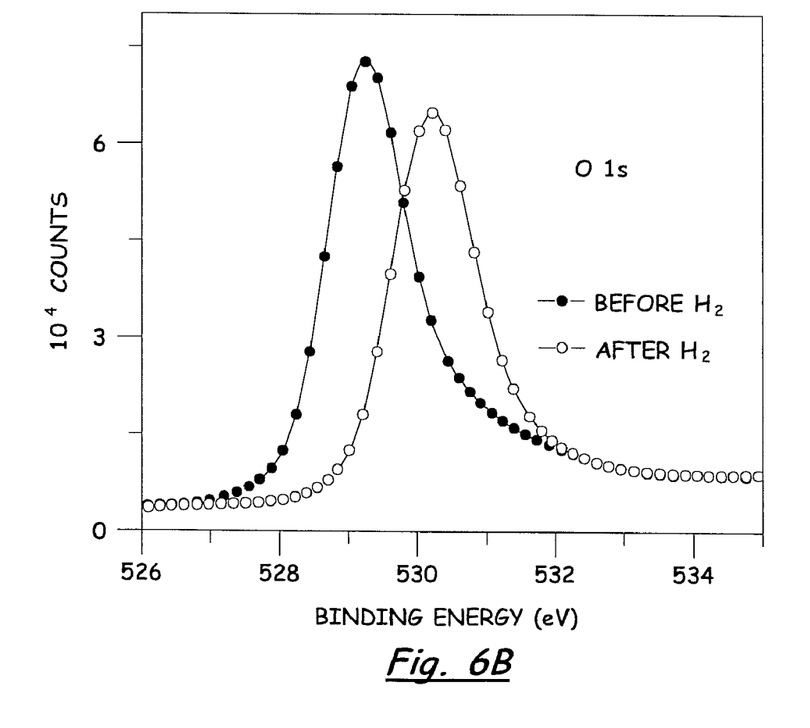

FIG. 6 shows that XPS spectra of the sample taken before and after the hydrogen treatment. FIG. 6 shows room-temperature XPS data showing the Fe 3p peak (upper portion, FIG. 6a) and the O 1s peak (lower portion. FIG. 6b) of the $Fe_2O_3$ pellet sample taken before and after the $H_2$ treatment at 575 K. The Fe $3p_{1/2}$ peak, which appears at 54.8 eV in fresh hematite, shows a clear shift to the higher energy side, 56.0 eV, after the hydrogen gas treatment, indicating that the chemical environment of the Fe ions underwent some change. The lack of any downward shift towards, and the absence of any new peaks formed at the Fe $3p_{1/2}$ peak position expected for Fe metal (53.2 eC), and/or maghemite (55.4 eV) or magnetite (53.9 eV) forms of iron oxide suggest that the observed increase in the sample magnetization with $H_2$ flow is most likely due to oxygen vacancies and rules out the formation of any other chemical phase. This is further confirmed by a slight upward shift of the O 1s peak after the $H_2$ treatment with no additional peaks or features. Adsorption of ions/molecules on the surface of the particles due to hydrogen interaction could also change the chemical environment of the oxygen and iron ions, although the TGA data favours the oxygen removal possibility.

In conclusion, we have shown for the first time known to the inventor that the magnetic properties of AF nanoparticles can be used as novel hydrogen sensing parameters. A preferred embodiment utilizes the effect of hydrogen interaction on the magnetic properties of nanoscale hematite. The magnetic parameters, saturation magnetization $M_s$ and remanence $M_r$, of nanoscale hematite scale well with the hydrogen gas flow rate and concentrations employed in this work. The results demonstrate that this new sensing method has sensitivity better than the explosive limit of 4% $H_2$ in air. While most of the experimental evidences of magnetic hydrogen sensing were obtained using a modified VSM setup, a simple and practical sensor is proposed based on the changes in the magnetic force exerted by the sample on a metal rod while hydrogen treatment changes the sample magnetization. Thermogravimetric analysis of the hematite sample showed significant mass loss when hydrogen gas was introduced, most of which was replenished when the gas was removed. XRD and XPS studies ruled out any impurity phase formation as a result of gas-sample interaction. The studies showed that the magnetic properties of AF nanoparticles can be used as novel hydrogen parameters, with hematite being the preferred example of AF nanoparticles.

Although this invention has been described above with reference to particular means, materials, and embodiments, it is to be understood that the invention is not limited to these disclosed particulars, but extends instead to all equivalents within the scope of the following claims.

The invention claimed is:

1. A magnetic reducing gas sensor comprising:
    a source of flowing reducing gas;
    a collection of antiferromagnetic nanoparticles configured as a film on a substrate;
    a heater adapted to heat the substrate;
    means for contacting the nanoparticles with the flowing gas; and
    means for detecting changes in the magnetic properties of the nanoparticles due to the effect of the flowing reducing gas.

2. The sensor of claim 1 wherein the reducing gas is hydrogen.

3. The sensor of claim 1 wherein the antiferromagnetic nanoparticles are hematite particles.

4. The sensor of claim 1 wherein the hematite particles are in the size of about 250 nm.

5. The sensor of claim 1 wherein the means for contacting the nanoparticles with the flowing gas comprises a hematite film.

6. The sensor of claim 1 wherein the means for detecting changes in the magnetic properties comprise a vibrating sample magnetometer (VSM).

7. A method for detecting the presence of a reducing gas, comprising:
    providing a collection of antiferromagnetic nanoparticles configured as a film on a substrate;
    heating the substrate to an elevated temperature;
    contacting the nanoparticles with a flowing reducing gas; and
    detecting a change in the magnetic properties of the nanoparticles as a result of their contact with the reducing gas.

8. The method of claim 7 wherein the reducing gas is hydrogen.

9. The method of claim 7 wherein the antiferromagnetic nanoparticles are hematite particles.

10. The method of claim 9 wherein the hematite particles are the size of about 250 nm.

11. The method of claim 7 wherein a change in the saturation magnetization of the nanoparticles is detected.

12. The method of claim 7 wherein a change in the remanence of the nanoparticles is detected.

* * * * *